United States Patent [19]

Nelson

[11] Patent Number: 4,711,966
[45] Date of Patent: Dec. 8, 1987

[54] PREPARATION OF ALKYL SILANES

[75] Inventor: Gunner E. Nelson, Baton Rouge, La.

[73] Assignee: Ethyl Corporation, Richmond, Va.

[21] Appl. No.: 27,897

[22] Filed: Mar. 19, 1987

[51] Int. Cl.$^4$ ................................................ C07F 7/08
[52] U.S. Cl. ................................................ 556/478
[58] Field of Search ...................................... 556/478

[56] References Cited

U.S. PATENT DOCUMENTS

| | | | |
|---|---|---|---|
| 2,857,414 | 10/1958 | Schmidt et al. | 556/478 X |
| 3,103,526 | 9/1963 | Jenkner | 556/478 X |
| 3,398,171 | 8/1968 | Giraitis et al. | 556/478 |
| 3,480,654 | 11/1969 | Sundermeyer et al. | 556/478 X |
| 4,367,343 | 1/1983 | Tamborski et al. | 556/478 X |
| 4,595,777 | 6/1986 | Bakshi et al. | 556/478 |

FOREIGN PATENT DOCUMENTS

| | | | |
|---|---|---|---|
| 825987 | 12/1959 | United Kingdom | 556/478 |
| 900132 | 7/1962 | United Kingdom | 556/478 |

OTHER PUBLICATIONS

Tamborski et al, Ind. Eng. Chem. Prod. Res. Dev. 22, 172-178 (1973).

*Primary Examiner*—Paul F. Shaver
*Attorney, Agent, or Firm*—Donald L. Johnson; John F. Sieberth; Robert A. Linn

[57] ABSTRACT

Mixtures of silahydrocarbons which comprise a product $RSiR'_3$, wherein R is an alkyl of 1-4 carbons, and R' is an alkyl of 8-14 carbons are produced by reacting a silicon tetrahalide, $SiX_4$, a trialkylaluminum, $R_3Al$, and an alkali metal aluminate $NaAlR'_4$. An alkali metal salt increases the relative amount of $RSiR'_3$ in the product. The trialkylaluminum can be replaced with an olefin or with an organoaluminum sesquihalide.

The products are useful as functional fluids.

8 Claims, No Drawings

PREPARATION OF ALKYL SILANES

CROSS REFERENCE TO RELATED APPLICATION

Subject matter of this application is related to my application Ser. No. 17, 852, filed Feb. 24, 1987, and entitled "Preparation of Alkyl Silanes".

FIELD OF THE INVENTION

This invention relates to the reaction of alkali metal aluminum tetraalkyls (also known as alkali metal aluminates) with trialkylaluminums and silicon tetrahalides. The invention also pertains to use of the alkylsilane products as functional fluids.

RELATED ART

Methods for the synthesis of tetraalkyl silanes include the reaction of alkyl magnesium halides or alkyl lithiums with halosilicon compounds; Tamborski et al U.S. Pat. No. 4,367,343, and Tamborski et al, Synthesis and Properties of Silahydrocarbons, A Class of Thermally Stable, Wide Liquid Range Fluids, *Ind. Eng. Chem. Prod. Res. Dev.* 22, 172–178 (1983).

British Pat. No. 825,987 to Kali-Chemie AG discloses the reaction of trialkylaluminums with alkyl- or arylchlorosilanes.

Jenkner, British Pat. No. 900,132, (also to Kali-Chemie) pertains to the reaction of sodium aluminum tetraethyl with halosilanes, such as silicon tetrachloride, where the reactants are used in a ratio of 4 to 1.

Bakshi et al, U.S. Pat. No. 4,595,777 pertains to the process of reacting an alkylchlorosilane with a trialkylaluminum.

Giraitis et al. U.S. Pat. No. 3,398,171, relates to the reaction of organosilanes and mixed metal compounds $AMR_n$ wherein A is an alkali metal and M can be aluminum. The process is conducted at a reaction temperature of $-20°$ C. to $+50°$ C.

SUMMARY OF THE INVENTION

This invention pertains to the preparation of tetraalkylsilanes, wherein one alkyl group is comparatively small and the other three are comparatively large. The small alkyl group has from one to about four carbon atoms, while the larger three groups have from about 8 to about 14 carbon atoms each. These products are prepared by a process which comprises reacting a trialkylaluminum, $AlR_3$, and an alkali metal aluminum tetraalkyl, $MAlR'_4$, with a silicon tetrahalide $SiX_4$, wherein X is a halide group. R is the smaller alkyl group (one to about four carbons) while R', is the larger. The process is conducted such that about ⅓ mole of $R_3Al$ and about ⅔ mole of metal tetraalkyl are reacted with each mole portion of silicon tetrahalide employed.

More particularly, in the process of this invention three moles of $MAlR'_4$ reactant combine with four moles of silicon tetrahalide reactant. In order to assist the reaction through the effect of mass action, an excess of $MAlR'_4$ can be utilized in the reaction mixture. For the process of this invention, one does not use a very large excess of $MAlR'_4$ reactant, since such excesses can cause the reaction to take a different course that for the purpose of this invention is not desired; cf, Jenkner, and Giraitis et al, supra.

In the process of this invention one mole of trialkylaluminum, $AlR_3$, is reacted with each three mole portion of $SiX_4$. Additional $AlR_3$ can be employed to assist the reaction through the effect of mass action; however, large excesses of trialkylaluminum are avoided since such excesses of this reactant can also cause the reaction to take a different course.

The process of this invention has several key features. First, all alkyl groups in the metal aluminate reactant, $MAlR'_4$ (except for those in the excess reactant employed) are utilized. Second, it is not necessary for purposes of economics to recycle alkyl aluminum values. Recycle of such compounds is very difficult (if not impossible) to accomplish at an acceptable cost, especially when the larger alkyl groups are of the preferred size for this invention ($C_8$–$C_{14}$), or larger. Third, when a silicon tetrachloride is used as a reactant in the process of this invention, inorganic co-product can be readily separated as a separate liquid phase. Fourth, this facilitates product workup.

The above-described process can be extended to other processes of this invention where an aluminate is formed containing the large and small groups in the proper proportions. The invention also comprises a process wherein a sesquihalide is used in place of the trialkylaluminum reactant.

Above it was stated that a key feature of this invention was the utilization of the alkyl groups in the $MAlR'_4$ reactant. Perhaps this can be better understood if the process of this invention is compared with processes of the prior art. In this regard the process of Jenkner (British No. 900,132) can be depicted by the following equation:

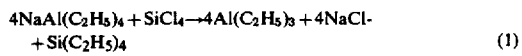

$$4NaAl(C_2H_5)_4 + SiCl_4 \rightarrow 4Al(C_2H_5)_3 + 4NaCl + Si(C_2H_5)_4 \tag{1}$$

As can be seen, most of the alkyl groups in the product remain bonded to aluminum, hence the Jenkner process is not as efficient as applicant's for transferring alkyl groups from aluminum to silicon. Also, a pertinent aspect of the Giraitis et al process can be represented by the following equation:

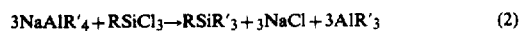

$$3NaAlR'_4 + RSiCl_3 \rightarrow RSiR'_3 + 3NaCl + 3AlR'_3 \tag{2}$$

Here again, most of the alkyl groups in the product mixture remain bonded to aluminum. Therefore, these prior art processes are much less efficient than the process of this invention. Therefore, the process of this invention represents a decided improvement in the art.

In the alkali metal aluminum tetraalkyls ($MAlR'_4$) used as reactants in the process of this invention, the organic radicals need not be the same. To prepare a reactant with dissimilar groups, one may react, for example, a metal aluminum hydride such as $NaAlH_4$ or $LiAlH_4$ with a mixture of olefins (such as a mixture of octene-1 and decene-1). This reaction may be conducted in accordance with the general procedure for preparing $MAlR'_4$ starting materials given below. Alternatively, one may use in the process of this invention a mixture of two or more metal aluminates wherein each one is prepared from a single olefin. Hence, in this invention there can be used, for example, a mixture of two aluminates such as $NaAl(C_8H_{17})_4$ and $NaAl(C_{10}H_{21})_4$. The ability to use a mixture of alkyl radicals as exemplified above is important, since a mixture can be chosen to produce a silane product with desired physical properties.

The use of the tri(loweralkyl) aluminum in the reaction mixture enables a significant amount of the product to have the formula RSiR'$_3$ wherein R is a lower alkyl and each of the three radicals depicted by R' are comparatively larger in size. Products of this type have physical properties desirable for use as functional fluids.

Products of this invention are useful as functional fluids with such diverse suggested uses as engine lubrication, electrical insulation, and heat transfer media. They can also be used as hydraulic fluids. The products of this invention are particularly useful under high temperature conditions where petroleum-based or synthetic hydrocarbon-based fluids cannot meet specifications. Product mixtures can be made to achieve desired rheological properties.

DESCRIPTION OF PREFERRED EMBODIMENTS

In a highly preferred embodiment this invention comprises a process for the preparation of a product comprising a tetralkylsilane,

wherein R and R' represent alkyl radicals such that R has up to about 4 carbon atoms, and the radicals represented by R' are alike or different and have from about 8 to about 14 carbon atoms; said process comprising reacting (a) a silicon tetrahalide having the formula SiX$_4$, wherein each X is a halide radical selected from the class consisting of fluoride, chloride and bromide, with (b) a trialkylaluminum R$_3$Al, and (c) an alkali metal aluminum tetralkyl reactant MAlR'$_4$, wherein M is selected from lithium, sodium, or potassium, said process being conducted at a temperature of from about 180° C. to about 230° C., and such that for each mole portion of SiX$_4$, there is employed about a $\frac{1}{3}$ mole portion of R$_3$Al, and about a $\frac{2}{3}$ mole portion of MAlR'$_4$.

As stated above, the process of this invention comprises a reaction of an alkali metal aluminate, MAlR'$_4$. Lithium, sodium and potassium aluminates can be used, with the lithium and sodium compounds being preferred. The sodium aluminates are highly preferred for reasons of economics and availability. Preferably, each radical indicated by R' in the formula MAlR'$_4$ is a hydrocarbyl, straight chain alkyl radical of about 8 to about 14 carbon atoms; however, it is to be understood that the radicals need not be limited to this structural configuration, and the size of the radicals can be larger or smaller than those within the preferred range.

The radicals of the preferred configuration and size appear to yield the more useful products, and they are preferred for that reason. However, any metal aluminate MAlR'$_4$ can be used for the process of this invention, so long as the radicals depicted by R' are stable under the reaction conditions employed, do not form an untoward amount of undesirable co-product when subjected to the reaction conditions employed, or unduly retard the reaction because of steric hindrance.

As mentioned above, the metal aluminate reactant may contain one or more groups indicated by R'. Alternatively, a mixture of metal aluminates can be used. The metal aluminate or aluminates need not be pure; for example, an aluminate can be used in the reaction mixture in which it is formed. Thus for example, Na, Al, and H$_2$ can be reacted in a hydrocarbon to form NaAlH$_4$ and the unisolated NaAlH$_4$ can be reacted with an olefin, such as octene—1, or a mixture of olefins, such as octene-1 and decene-1 in a mole ratio of 2 to 1, and the resultant reaction mixture used as a reactant in the process of this invention. When the reactant is formed in this way, the olefin is generally used in excess. Consequently, the reactant mixture used in the instant process can frequently contain an olefin, or mixture of olefins.

Most olefins available in large commercial quantities are made from natural products or by chain growth of ethylene. In either case, the olefin usually has an even number of carbon atoms. However, it is to be understood that an even number of carbon atoms is not critical, and MAlR'$_4$ reactants with one or more R' radicals having an odd number of carbon atoms can also be used in this invention. Nevertheless, because of the more ready availability of even numbered olefins, the preferred MAlR'$_4$ reactants for this invention have alkyl radicals (depicted by R') that are derived from one or more of the following olefins:

octene-1
decene-1
dodecene-1
tetradecene-1
hexadecene-1

As stated above, the process of this invention comprises use of a trialkylaluminum, R$_3$Al, wherein the radicals depicted by R are lower alkyl. Although each R may be methyl, ethyl, or a propyl or butyl radical, ethyl is preferred. Preferably, each R is the same; thus, triethylaluminum is a highly preferred reactant for this invention.

The other reactant employed in the process of this invention is a silicon tetrahalide, SiX$_4$. The four groups indicated by X are halide radicals; preferably all four are the same; however, reactants with two or three different halo groups per molecule can be used. More preferably, the halide groups are chloro or bromo radicals, most preferably they are all chloro groups. Thus silicon tetrachloride, SiCl$_4$, is a highly preferred reactant for this invention.

The process of this invention is conducted using a temperature that is high enough to cause the reaction to take place at a reasonable rate, but not so high that it causes an undesirable amount of side reaction or decomposition to occur. Generally speaking, a temperature above 150° C. and below 230° C. is used. Preferably, the temperature is from about 180° C. to 200° C.

The reaction time is not a truly independent variable but depends at least to some extent on the other reaction conditions employed such as the reaction temperature. Generally speaking, reaction is essentially complete in from about 3 to 10 hours with 5 to 6 hours being typical.

Where a gaseous or low boiling ingredient is not used, the reaction pressure does not have a large effect on the course of the reaction. Atmospheric, sub-atmospheric and super atmospheric pressure can be used. Atmospheric pressure or the autogenous pressure of the system are preferred. However, a reaction with ethylene is described below. It illustrates that high pressures can be used.

Although the process of this invention is preferably conducted using alkali metal aluminates, MAlR'$_4$, such as described above, it is to be borne in mind that similar reactants can also be used in this invention in substantially the same way, to produce substantially the same results. Thus for example, one may use alkaline earth aluminates, M'(AlR'$_4$)$_2$, wherein M' is Mg, Ca or Ba. When these materials are used in the process of this invention, one-half of the molar quantities described above for MAlR'$_4$ reactants are employed, since each molecule of the alkaline earth compounds contains two, i.e. twice, as many (AlR'$_4$) groups. One may use as a reactant a compound having the formula R"$_3$Al wherein R" is an alkyl group that has 5 or more carbon atoms.

Optionally, the product of this invention can be conducted in the presence of an alkali metal salt, e.g. the halides. Such salts are exemplified by the sodium compounds NaF, NaCl and NaBr. It has been found that use of sodium chloride in about an equimolar portion with the trialkylaluminum assists formation of RSiR'$_3$ product. (It is believed that the metal halide and trialkylaluminum can interact to form a material exemplified by NaAlR'$_3$Cl, and that this species may be involved in enhancing the reaction.

It is not necessary to employ the metal halide in the molar amount mentioned above; greater and lesser amounts can be used. A skilled practitioner can readily determine the lower limit in the amount of metal halide to be employed—it is the least amount which gives an increase in relative amount of RSiR'$_3$ product, under the reaction conditions employed.

Preferably, more than the amount of metal halide required to give the desired result is not used. An excess wastes material, and can make product isolation and workup more difficult. Thus, although there is no real upper limit in the amount of halide to be employed, a skilled practitioner (1) uses an amount which gives the desired relative increase in RSiR'$_3$ product, and (2) preferably avoids use of additional halide which does not afford the increase, and/or unduly complicates product isolation or workup.

General Procedure (A) Preparation of tetralkylaluminate reactant

Lithium aluminum hydride reacts with olefins at about 110°–120° C. forming complexes with the structure LiAlR$_4$. Sodium aluminum hydride is not added to olefins even at 180° C. without the presence of catalytic amounts of a material selected from trialkylaluminums, dialkyl aluminum hydrides, lithium aluminum hydride, or aluminum, zinc or lithium halide. The first three hydrogens are readily replaced at 80°–130° C., but the fourth requires a temperature of 170°–230° C. or thereabouts, for about 3 to 6 hours. The process is preferentially conducted in the presence of an excess of olefin, e.g. a 1:8 mole ratio of NaAlH$_4$ to olefin, and 5–15 mole % (based on NaAlH$_4$) of the catalyst. A paraffin diluent can be used in the reaction mixture.

Alternatively, triethylaluminum or similar organoaluminum having alkyl groups of 1–4 carbons can be used as catalyst for the formation of the aluminate and as the reactant. In this manner, a methyl group can be introduced into the final product by using trimethyl aluminum or methyl aluminum sesquihalide. In this manner the overall process is simplified by elimination of one catalyst, e.g. the lithium catalyst used in the formation of the aluminate.

As an illustration of the preparation of NaAlR'$_4$, a reactor is charged with NaAlH$_4$, catalyst, and olefin in the above-defined relative amounts and heated for 1–2 hours at 125° C., followed by 3–4 hours at 175° C. (It is believed the duration of the heating cycle can be reduced somewhat.) The product is discharged after cooling. The final product typically contains 30–65% of NaAlR$_4$, and is suitable for many reactions. It is not necessary that the aluminate be employed in the product mix; if desired it can be isolated from some or all of the other substances present in the resultant reaction mixture. Concentrated solutions can be diluted and used, if desired.

The following illustrates how to conduct the process of this invention:

A sodium aluminate (NaAlR'$_4$) solution is added to a suitable reaction vessel. To the NaAlR'$_4$ reactant is added an aluminum trialkyl, R$_3$Al. (There is some evidence that these materials can interact at least to some extent in a manner illustrated by the following equation. In the equation, Et represents the ethyl radical and R' represents a dissimilar alkyl group; i.e. one having about 8–14 carbons.

$$4Et_3Al + 3NaAlR'_4 \rightarrow 3NaAlEt_4 + 4R'_3Al \qquad (3)$$

Partial, rather than the full exchange of the alkyl groups depicted by the equation, may also occur.)

To the mixture formed by intermixing the R$_3$Al and NaAlR'$_4$ reactants is added the SiX$_4$ reactant, e.g. SiCl$_4$. The mole ratio of reactants is within the ranges given below

| | |
|---|---|
| SiX$_4$ | 1.0 mole |
| NaAlR'$_4$ | 0.75–1.0 mole |
| R$_3$Al | 0.33–0.50 mole. |

Preferably, the ratio of the combination of aluminum containing reactants to the silicon tetrahalide is within the range of 10 (aluminum reactants) to 1.0 (SiX$_4$) to 1.25 (aluminum reactants) to 1.0(SiX$_4$). In other words the Al/Si ratio preferably is from equimolar to a 25% excess of aluminum.

The reaction mass is heated to about 190° C. for 2–6 hours, with efficient stirring.

Product workup is conducted as follows:

The mixture is hydrolyzed with 3N HCl and washed with the HCl and then with H$_2$O. The organic phase (which contains the product) is separated and dried, e.g. over anhydrous K$_2$CO$_3$ or MgSO$_4$. The products of this invention may be vacuum stripped to remove undesirable light ends. Vacuum stripping can be conducted at about 0.5 mm Hg and at about 190° C. Vacuum stripping is especially helpful when the product mixture is intended for use as a functional fluid. The above-described product workup can be conducted by two related, alternative procedures. As described above, the entire reaction product can be utilized in the workup. This method is convenient for small scale, laboratory preparations. Alternatively, before product workup, the inorganic co-product can be separated from the organic layer. In this alternative method, the workup procedure is conducted on the organic fraction after separation of the inorganic co-product.

EXAMPLE 1

A reaction vessel was charged with a mixture of:
33.86 millimoles of NaAl(C$_8$H$_{17}$)$_2$(C$_{10}$H$_{21}$)$_2$
15.0 millimoles of triethylaluminum, and
45.16 millimoles of SiCl$_4$.

The resultant mixture was reacted by stirring at 190° C. for five hours. Gas chromatography showed there were numerous products. Products having the formula $(C_2H_5)Si(C_8H_{17})_m(C_{10}H_{21})_{3-m}$ were noted along with lighter and heavier components.

EXAMPLE 2

To a suitable reaction vessel was charged:
- 37.5 millimoles of sodium aluminum tetraoctyl in an octene-1 solution
- 20.0 millimoles of triethylaluminum (TEA), and
- 50.0 millimoles of SiCl$_4$.

(This mixture represents about a 20% molar excess of TEA calculated as follows, using 16.7 millimoles as the amount theoretically required to have the mole ration of TEA to SiCl$_4$ be 0.33 to 1.0).

$$\frac{20 - 16.7}{16.7} = 19.8\%$$

The mole ratio of the metal aluminate to SiCl$_4$ is 37.5/50 or (0.75 to 1.0).

The reaction was conducted with stirring for five hours at 190° C. Gas chromatographic/mass spectrophotometric (GC/MS) analysis indicated that the following were present in the reaction mixture:

| PRODUCT | |
|---|---|
| Compound | Area % |
| $(C_2H_5)_3Si(C_8H_{17})$ | 6.1 |
| C$_8$ dimer | 6.0 |
| $(C_2H_5)_2Si(C_8H_{17})_2$ | 17.77 |
| $(C_2H_5)Si(C_8H_{17})_3$ | 28.35 |
| $Si(C_8H_{17})_4$ | 20.14 |
| unidentified products | 3.1 |

(Heptane was used as the solvent when the flash stripped product was submitted for GC/MS.)

The total weight of product after final strip was 17.8 g. Assuming that the product had an average molecular weight of 396, i.e. the molecular weight of $(C_2H_5)Si(C_8H_{17})_3$, this represents a yield of 90.8%.

EXAMPLE 3

To a suitable reaction vessel was charged:

| 79 millimoles | NaAl(C$_8$H$_{17}$)$_4$ |
|---|---|
| 33 millimoles | (C$_2$H$_5$)$_3$Al |
| 33 millimoles | NaCl |
| 94.8 millimoles | SiCl$_4$ |

In this reaction mixture there was an excess of aluminum reactants calculated as follows:

(A) Mole % excess NaAl(C$_8$H$_{17}$)$_4$ 94.8 × ¾ = 71.1 millimoles NaAl(C$_8$H$_{17}$)$_4$
(79 − 71.1) ÷ 71.1 = 11.1 mole % excess (B) Mole % excess (C$_2$H$_5$)$_3$Al 4.8 × ¼ = 31.6 millimoles (C$_2$H$_5$)$_3$Al
(33 − 31.6) ÷ 31.6 = 4.4 mole % excess Assuming the molecular weight of product was 396, the overall yield was 73%. Analysis by GC/MS gave the results in the table below. In the table, the analysis is compared with analytical results obtained on the product mixture obtained by the process of Example 2.

| Compound | Example 3 Mole % | Example 2 Mole % |
|---|---|---|
| $(C_2H_5)_3Si(C_8H_{17})$ | 10.4 | 13.3 |
| $(C_2H_5)_2Si(C_8H_{17})_2$ | 24.3 | 28.7 |
| $(C_2H_5)Si(C_8H_{17})_3$ | 46.9 | 36.6 |
| $Si(C_8H_{17})_4$ | 18.4 | 31.3 |
| | 100.0 | 99.9 |

The comparison indicates that NaCl favors production of $(C_2H_5)$ $Si(C_8H_{17})_3$.

The reaction mixture of this Example 3 was subjected to a vacuum strip using a bath temperature of 190° C., at 0.5 mm Hg until substantially all light materials were removed. The isolated product weighed 25.4 grams and had the following composition. In the following table, the product mixture is compared with that obtained upon vacuum strip of the Example 2 product. The vacuum operation for that product involved conditions similar to those mentioned above.

| VACUUM STRIPPED PRODUCT | | |
|---|---|---|
| Compound | Example 3 Mole % | Example 2 Mole % |
| $(C_2H_5)_3Si(C_8H_{17})$ | 0.0 | 5.1 |
| $(C_2H_5)_2Si(C_8H_{17})_2$ | 26.4 | 30.6 |
| $(C_2H_5)_2Si(C_8H_{17})_3$ | 52.7 | 40.3 |
| $Si(C_8H_{17})_4$ | 20.8 | 24.0 |
| | 99.0 | 100.0 |

The process of this example can be repeated using a reaction temperature of from about 150° C. to about 230° C. and a reaction time of three to ten hours. It can be repeated using trimethylaluminum, tri-n-propylaluminum or tri-n-butylaluminum in place of the triethylaluminum. These substances can be substituted in the above example in a ratio of 0.33 to 0.50 mole, per 1.0 mole of SiX$_4$ reactant. The corresponding methyl-, propyl-, or butyl- products are obtained. The process of the above example can also be repeated using as the NaAlR'$_4$ reactant, the compounds wherein each of the four R' radicals are decyl, dodecyl, or tetradecyl, and the mole ratio of NaAlR'$_4$ reactant to SiCl$_4$ is from (0.75 to 1.0) to (1.0 to 1.0). The corresponding products are obtained. In the process of the above example, SiF$_4$ or SiBr$_4$ can be substituted for the SiCl$_4$ employed. The process can also be repeated using NaF or NaBr instead of the NaCl employed.

EXAMPLE 4

The following change was added to a suitable reaction vessel:

| Compound | Millimoles |
|---|---|
| NaAl(C$_8$H$_{17}$)$_4$ | 43.6 |
| NaAl(C$_{10}$H$_{21}$)$_2$ | 10.9 |
| (C$_2$H$_5$)$_3$Al | 25.7 |
| NaCl | 60.0 |
| SiCl$_4$ | 68.5 |
| nonane | ~30.0 |

This mixture was reacted with stirring at 90° C. It was then hydrolyzed with 50 mL 3N HCl, and then washed successively with 50 mL portions of 3N HCl and H$_2$O. The washed product was dried over anhydrous K$_2$CO$_3$. Gas chromatography showed the product mixture to be a typical $Et_{0.2}SiOct_{0.4}Dec_{0.4}$ product (Et=Ethyl, Oct=octyl, Dec=decyl).

The residue after the vacuum strip weighed 19.6 grams. Assuming an average molecular weight of 412.8 $(Et)Si(Oct)_{2.4}(Dec)_{0.6})$ the yield was 69.2% based on $SiCl_4$.

EXAMPLE 5

Suitable reaction vessel was charged with:

| Compound | Millimoles |
|---|---|
| $NaAl(C_8H_{17})_4$ | 50.56 |
| $NaAl(C_{10}H_{21})_2$ | 10.11 |
| $(C_2H_5)_3Al$ | 27.8 |
| NaCl | ~40.0 |
| $SiCl_4$ | 75.8 |

The two sodium aluminates were added as 35% solutions in the corresponding olefin. The reaction mass was heated at 190° C. for five hours with stirring. The reaction vessel was rinsed with heptane to aid in removal of the crude product mixture. The mixture was hydrolyzed with 3N HCl, then washediwth two 125 mL portions of 3N HCl and finally with two 300 mL portions of $H_2O$. The resultant mixture was then dried over $MgSO_4$. After filtration, it was striped under vacuum. Final strip conditions were 0.5 mm and 190° C. The reaction mixture weighed 26.6 grams. Analysis by GC indicated the following:

| Product | Area % |
|---|---|
| $(C_2H_5)_2Si(C_8H_{17})_2$ | 8.78 |
| $(C_2H_5)_2Si(C_8H_{17})(C_{10}H_{21})$ | 5.89 |
| $(C_2H_5)_2Si(C_{10}H_{21})_2$ | 2.24 |
| $(C_2H_5)Si(C_8H_{17})_3$ | 21.77 |
| $(C_2H_5)Si(C_8H_{17})_2(C_{10}H_{21})$ | 13.71 |
| $(C_2H_5)Si(C_8H_{17})(C_{10}H_{21})_2$ | 2.94 |
| $(C_8H_{17})_4Si$ | 15.64 |
| $(C_8H_{17})_3Si(C_{10}H_{21})$ | 12.19 |
| $(C_8H_{17})_2Si(C_{10}H_{21})_2$ | 3.70 |
| Heavies | 2.94 |
| | 89.80 |

Products of this invention are useful as functional fluids. As a demonstration of this, the vacuumed stripped products of Examples 2, 3 and 5 were submitted for viscosity measurements. The values obtained are reported in the following table. The results indicate that the two silahydrocarbon mixtures approximate U.S. Air Force synthetic lube specifications:

| Viscosity of $Et_{0.2}Si(Oct)_{0.4}(Dec)_{0.4}$ Preparations | | | |
|---|---|---|---|
| | Centistokes | | |
| | −54° C. | 38° C. | 204.0° C. |
| Air Force Specification Preparations | 2500 max | 9.5 min | 0.9 min |
| Example 2 | 1770 | 8.12 | 0.826 |
| Example 3 | 2000 | 8.94 | 0.866 |
| Example 5 | 2510 | 11.0 | 0.96 |

This suggests that products of this invention are useful as hydraulic fluids in military or other applications. Some of these products are preferably used in applications where the high temperature viscosity requirements are not as severe as set forth by the Air Force.

Hydraulic fluids are used in hydraulic systems to transmit pressure or energy. They also serve to reduce friction in bearings and between sliding surfaces in pumps and similar articles. Hydraulic and other functional fluids also protect surfaces from rusting, and can remove undesirable particulate matter away from surfaces.

Like other functional fluid base stocks, the silahydrocarbons produced by the process of this invention can be admixed with additives such as rust inhibitors, antiwear agents, corrosion inhibitors and the like.

The oxidative stability of fluids of this invention can be increased by removing residual olefin linkages in the reaction products formed by the process described above. Olefinic linkages can be removed by fractional distillation or hydrogenation.

The process of this invention can be extended as demonstrated by the following example. As can be seen, this extension exemplifies a two step process in which sodium aluminate is first produced. Subsequently, the product is reacted with ethylene to form a product mixture of this invention. As reported, the reaction with ethylene is not complete at a lower temperature as shown by the empirical formula given below in which 0.63 mole of hydrogen is present. After reaction with more ethylene at 170° C., the hydrogen content was materially reduced. However some of the ethylene dimerized, and this was the source of the butyl groups identified in the product mixture.

EXAMPLE 6

An autoclave was charged with:

| Compound | Weight in Grams | Millimoles |
|---|---|---|
| $NaAlH_4$ | 22.6 | 0.397 |
| toluene | 25 | |
| octene/decene | 146 | |

In addition, 146.1 grams of a 5/1 mixture of octene-1 and decene-1 (1.25 mole), and 5.4 mL of triethylaluminum (0.397 millimole) were added. The resultant mixture was then heated with stirring for three hours at 125° C. Thereafter, the vessel was pressured to 750 psi with ethylene. After three hours, no ethylene consumption was observed. The reaction mixture was cooled, vented and sampled for analysis. Analysis indicated the composition of the metal aluminate to be $NaAlR_{3.1}H_{0.63}Et_{0.27}$.

The next day, the reaction vessel was sealed, heated to 170° C., and pressured to 800 psi with ethylene. The pressure dropped to 600 psi over two hours. More ethylene was added to increase the pressure to 750 psi, and another pressure drop to 525 psi was noted (over 1½ hours).

The reaction mass was cooled, vented and sampled for analysis. It indicated that the aluminate composition was $NaAlR_{3.1}Et_{0.08}Bu_{0.08}H_{0.01}$, and that the aluminate concentration was 47.5%.

The product was stripped under 100 mm Hg at 100° C. to remove toluene.

A mixture of the aluminate product thereby produced, 76.0 grams (95.1 millimoles), with 19 grams of octane, and 15.4 grams of $SiCl_4$ (90.6 millimoles) was then reacted at 190° C. for five hours. The resultant crude, organic product was hydrolyzed and washed with 3N HCl, and then washed with water and dried over $MgSO_4$. After vacuum strip, 31.4 grams of product mixture comprising tetraalkyl silanes, was obtained. The product was polish filtered and submitted for viscosity measurements. The following results were obtained.

| Temperature | Viscosity in Centistokes |
|---|---|
| −54° C. | * |
| 38° C. | 10.6 |
| 204° C. | 1.0 |

*The product was solid at −54° C.

The process of this example can be extended to the use of higher olefins such as those having 3 or 4 or more carbon atoms. These olefins can be reacted with the other reactants in the foregoing description using the reaction conditions above described. Similar results are obtained.

The olefin pressure used is preferably 600–1500 psi; however, higher and lower pressures can be used.

The process of this invention can also be extended to the use of an aluminum sesquihalide in place of the trialkylaluminum described above. Although not bound by any theory, it is believed that this modification can be illustrated by the following equation wherein Me$_3$Al$_2$Cl$_3$ is used to depict methyl aluminum sesquichloride:

$$9NaAl(C_8H_{17})_4 + 4Me_3Al_2Cl_3 + 12SiCl_4 + 8NaCl \rightarrow 12MeSi(C_8H_{17})_3 + 17NaAlCl_4 \quad (4)$$

EXAMPLE 7

A suitable reaction vessel was charged with the following:

| Compound | Millimoles |
|---|---|
| NaAl(C$_8$H$_{17}$)$_4$ | 56.2 (in an octene-1 solution comprising 2.85 weight % aluminum) |
| (CH$_3$)$_3$Al$_2$Cl$_3$ | 25 |
| SiCl$_4$ | 85.2 (14.5 g) |

In addition, 20 mL of octane, and 2.92 grams of NaCl was added to the reaction mixture. The resultant reaction mixture was reacted at 190° C. for five hours. After cooling, the mixture was hydrolyzed with 3N HCl as before. Considerable "rag " layer was noted and this was taken as an indication of incomplete alkylation. The organic phase plus C$_8$ paraffin diluent was dried over MgSO$_4$. Gas/liquid chromatography showed the following:

| Product | Mole Fraction | Mole Ratio |
|---|---|---|
| (CH$_3$)$_2$Si(C$_8$H$_{17}$)$_2$ | 0.285 | 1.0 |
| CH$_3$Si(C$_8$H$_{17}$)$_3$ | 0.338 | 1.18 |
| (C$_8$H$_{17}$)$_4$Si | 0.376 | 1.32 |
|  | 0.999 |  |

After a vacuum strip, 24.2 grams of product were obtained. Analysis by GLC showed about 88 area % for the sum of the three products given above, or an (approximate) 75% yield.

The process of this example can be carried out using other sesquihalides such as (C$_2$H$_5$)$_3$Al$_2$Cl$_3$, (C$_3$H$_7$)$_3$Al$_2$Cl$_3$ and (C$_4$H$_9$)$_3$Al$_2$Cl$_3$. These materials can be reacted with the other reactants described in the foregoing description using the reaction conditions above described. Similar results are obtained. A skilled practitioner may make substitutions or modifications (within the skill of the art) in light of the above, detailed description of this invention. Such extensions are to be considered within the spirit and scope of the claims that follow.

I claim:

1. A process for preparing a product composition comprising a compound having the formula RSiR'$_3$ wherein R is a lower alkyl radical of 1–4 carbon atoms, and each R' is an alkyl radical of from about 8 to about 14 carbon atoms, said process comprising reacting (a) a silicon tetrahalide having the formula SiX$_4$, wherein each X is a halide radical selected from the class consisting of fluoride, chloride and bromide, with (b) a trialkylaluminum R$_3$Al, and (c) an alkali metal aluminum tetraalkyl MAlR'$_4$ reactant, wherein M is selected from lithium, sodium, or potassium, said process being conducted at a temperature of from about 80° C. to about 230° C., and such that for each mole portion of SiX$_4$, there is employed about a ⅓ mole portion of R$_3$Al, and about a ¾ mole portion of MAlR'$_4$.

2. A process of claim 1 being conducted in the presence of a quantity of an alkali metal halide MX sufficient to increase the amount of RSiR'$_3$ relative to the amount of R$_2$SiR'$_2$ in said product composition.

3. A process of claim 1 wherein said trialkylaluminum is triethylaluminum.

4. A process of claim 2 wherein said metal halide is sodium chloride.

5. A process of claim 1 wherein said silicon tetrahalide is silicon tetrachloride.

6. A process for preparing a product composition comprising a compound having the formula RSiR'$_3$ wherein R is a lower alkyl radical of 2–4 carbon atoms, and each R' is an alkyl radical of from about 8 to about 14 carbon atoms, said process comprising reacting (a) a silicon tetrahalide having the formula SiX$_4$, wherein each X is a halide radical selected from the class consisting of fluoride, chloride and bromide, with (b) an olefin having 2–4 carbon atoms, and (c) an alkali metal aluminum tetraalkyl MAlR'$_4$ reactant, wherein M is selected from lithium, sodium, or potassium, said process being conducted at a temperature of from about 180° C. to about 230° C., and such that for each mole portion of SiX$_4$, there is employed about a ¼ mole portion of olefin, and about a ¾ mole portion of MAlR'$_4$.

7. A process for preparing a product composition comprising a compound having the formula RSiR'$_3$ wherein R is a lower alkyl radical of 1–4 carbon atoms, and each R' is an alkyl radical of from about 8 to about 14 carbon atoms, said process comprising reacting (a) a silicon tetrahalide having the formula SiX$_4$, wherein each X is a halide radical selected from the class consisting of fluoride, chloride and bromide, with (b) an aluminum sesquihalide R$_3$Al$_2$Cl$_3$, and (c) an alkali metal aluminum tetraalkyl MAlR'$_4$ reactant, wherein M is selected from lithium, sodium, or potassium, said process being conducted at a temperature of from about 180° C. to about 230° C., and such that for each 12 mole portion of SiX$_4$, there is employed about a 4 mole portion of said sesquihalide, and about a 9 mole portion of MAlR'$_4$.

8. The process of claim 7 being conducted in the presence of about 8 moles of alkali metal halide.

* * * * *

UNITED STATES PATENT AND TRADEMARK OFFICE
CERTIFICATE OF CORRECTION

PATENT NO. : 4,711,966　　　　　　　　　　　Page 1 of 2
DATED : December 8, 1987
INVENTOR(S) : GUNNER E. NELSON It is certified that error appears in the above-identified patent and that said Letters Patent is hereby corrected as shown below:

Column 2, line 43, reads "$_3$NaCl" and should read -- 3NaCl --.

Column 6, line 37, reads "10" and should read -- 1.0 --.

Column 7, line 62, reads "4.8" and should read -- 94.8 --.

Column 8, line 30, reads "99.0" and should read -- 99.9 --.

Column 9, line 8, reads "Suitable" and should read -- A suitable --.

Column 9, line 23, reads "washediwth" and should read -- washed with --.

Column 9, line 26, reads "striped" and should read -- stripped --.

Column 10, line 56, reads "$NaAlR_{3.1}Et_{0.08}Bu_{0.08}H_{0.01}$" and should read -- $NaAlR_{3.1}Et_{.81}Bu_{.08}H_{.01}$ --.

UNITED STATES PATENT AND TRADEMARK OFFICE
CERTIFICATE OF CORRECTION

PATENT NO. : 4,711,966

DATED : December 8, 1987

INVENTOR(S) : GUNNER E. NELSON

It is certified that error appears in the above-identified patent and that said Letters Patent is hereby corrected as shown below:

Column 11, line 24, reads "$All_2Cl_3$" and should read -- $Al_2Cl_3$ --.

Column 11, line 27, reads "$NaAlCl_{14}$" and should read -- $NaAlCl_4$ --.

Signed and Sealed this

Twenty-eighth Day of June, 1988

Attest:

DONALD J. QUIGG

*Attesting Officer*   *Commissioner of Patents and Trademarks*